United States Patent
Morikawa et al.

(10) Patent No.: US 8,355,505 B2
(45) Date of Patent: Jan. 15, 2013

(54) PICTURE TAKING APPARATUS AND METHOD OF CONTROLLING SAME

(75) Inventors: Goichi Morikawa, Kanagawa (JP); Go Tokura, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1095 days.

(21) Appl. No.: 11/865,165

(22) Filed: Oct. 1, 2007

(65) Prior Publication Data

US 2008/0025574 A1    Jan. 31, 2008

Related U.S. Application Data

(62) Division of application No. 10/460,268, filed on Jun. 13, 2003, now Pat. No. 7,305,089.

(30) Foreign Application Priority Data

Jun. 20, 2002 (JP) ................................. 2002-180048

(51) Int. Cl.
*H04N 7/167* (2011.01)

(52) U.S. Cl. .......... 380/210; 380/54; 380/252; 380/287; 713/176; 348/231.3; 348/239; 382/115

(58) Field of Classification Search ................. 380/210, 380/54, 252, 287; 713/176; 348/231.3, 239; 382/115
See application file for complete search history.

(56) References Cited

U.S. PATENT DOCUMENTS

| 5,530,759 | A | | 6/1996 | Braudaway et al. ............ 380/54 |
| 5,995,630 | A | * | 11/1999 | Borza ............................. 380/54 |
| 6,011,860 | A | | 1/2000 | Fujieda et al. ................. 382/126 |
| 7,043,048 | B1 | * | 5/2006 | Ellingson ...................... 382/100 |
| 7,047,418 | B1 | | 5/2006 | Ferren ........................... 713/186 |
| 7,162,475 | B2 | * | 1/2007 | Ackerman ............................ 1/1 |
| 7,197,157 | B2 | | 3/2007 | Akashi .......................... 382/100 |
| 2003/0105721 | A1 | * | 6/2003 | Ginter et al. .................... 705/54 |
| 2003/0200217 | A1 | * | 10/2003 | Ackerman ........................ 707/9 |
| 2003/0235411 | A1 | | 12/2003 | Morikawa et al. ............ 396/281 |
| 2005/0036656 | A1 | * | 2/2005 | Takahashi ..................... 382/100 |

FOREIGN PATENT DOCUMENTS

| JP | 7-323008 | 12/1995 |
| JP | 8-504979 | 5/1996 |
| JP | 8-241403 | 9/1996 |
| JP | 10-056610 | 2/1998 |
| JP | 10-150517 | 6/1998 |

(Continued)

OTHER PUBLICATIONS

Japanese Office Action issued Jan. 16, 2009, in Japanese Application No. 2002-180048.

*Primary Examiner* — April Shan

(74) *Attorney, Agent, or Firm* — Fitzpatrick, Cella, Harper & Scinto

(57) ABSTRACT

The camera includes a sensor for sensing the photographer's iris image and registering the image in advance. The iris image is recorded in the image of a subject by a digital MCU at a timing different from that at which the image of the subject is captured. The recording timing is that at which the camera power supply is turned off, that at which a recording medium is ejected from the camera or that at which the iris image to be recorded is changed to changed to the registered iris image of another photographer. The recording of the iris image is achieved by embedding it as a watermark or by appending it to metadata.

18 Claims, 13 Drawing Sheets

FOREIGN PATENT DOCUMENTS

| | | |
|---|---|---|
| JP | 10-289304 | 10/1998 |
| JP | 10-290359 | 10/1998 |
| JP | 11-313237 | 11/1999 |
| JP | 2000-196998 | 7/2000 |
| JP | 2000-295458 | 10/2000 |
| JP | 2002-95458 | 10/2000 |
| JP | 2001-069454 | 3/2001 |
| JP | 2001-094847 | 4/2001 |
| JP | 2001-144937 | 5/2001 |
| JP | 2002-016791 | 1/2002 |
| WO | WO 94/09446 | 4/1994 |

* cited by examiner

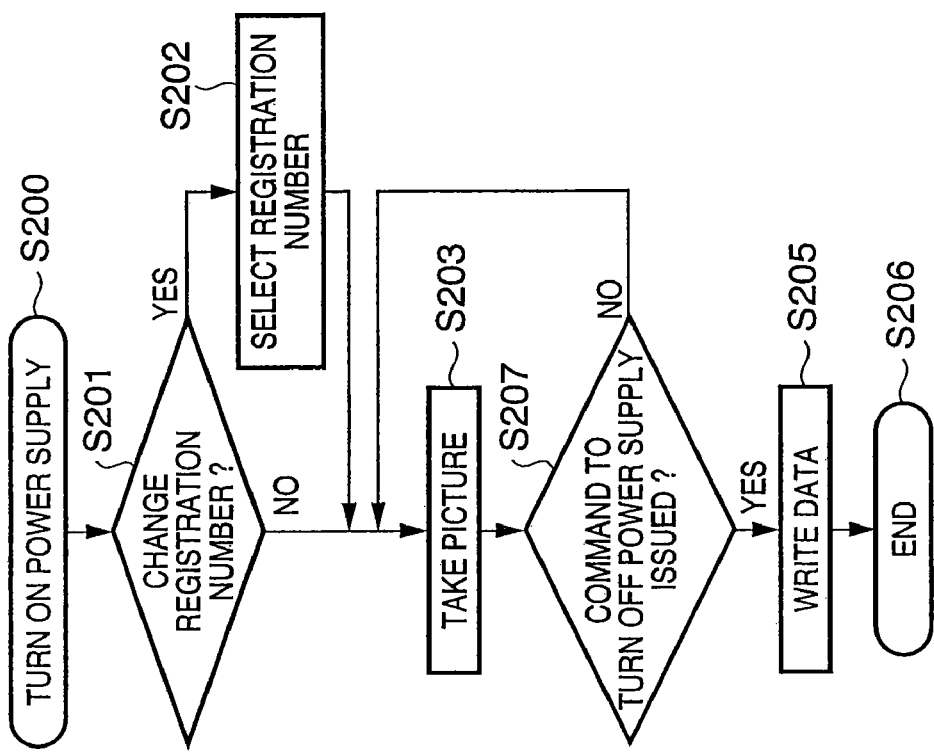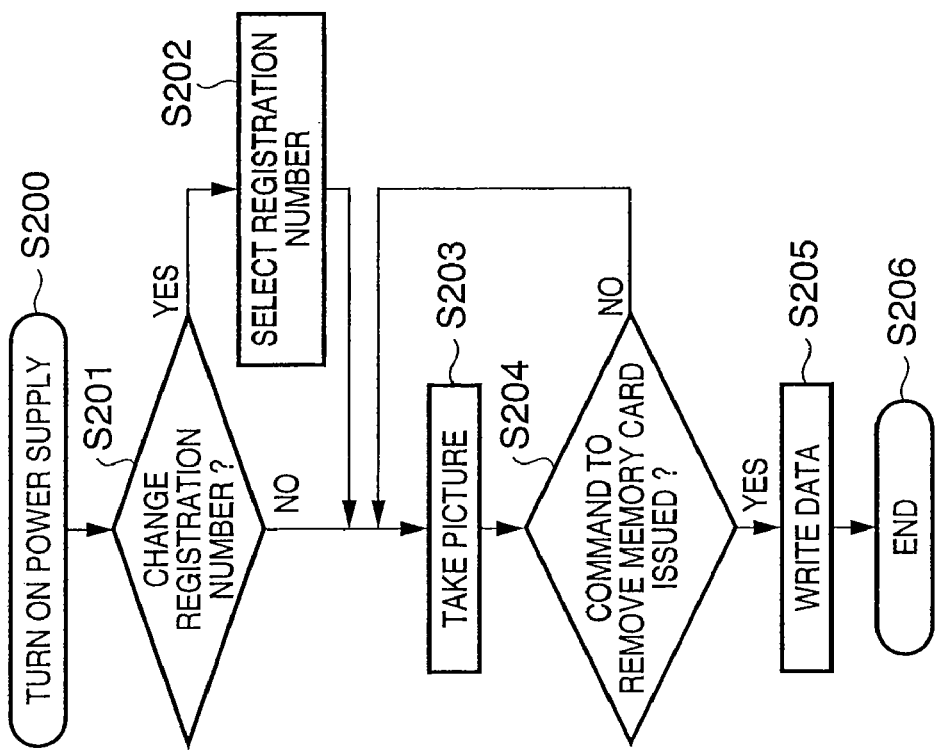

PICTURE TAKING APPARATUS AND METHOD OF CONTROLLING SAME

The present application is a divisional of U.S. application Ser. No. 10/460,268 filed Jun. 13, 2003, pending.

FIELD OF THE INVENTION

This invention relates to an imaging apparatus for electrically taking the image of a subject. More particularly, the invention relates to an imaging apparatus with which it is possible to protect the copyright of the photographer.

BACKGROUND OF THE INVENTION

Digital still cameras and digital video cameras that have become increasingly popular in recent years convert an image signal, which is the result of sensing an image by an image sensing device such as a CCD sensor, to image data in a digital format and store this image data on a recording medium such as a memory card.

Such digital image data can readily be corrected, manipulated and printed by a computer and has come to be utilized in the ordinary home. At the same time, owing to the spread of networks, particularly the Internet, it is now easy for digital image data to be circulated among an unspecified number of users.

Against this background, the necessity for imaging apparatus such as digital still cameras and digital video cameras has grown explosively.

The widespread use of personal computers and the like has made the copying of digital data easier and less expensive. In addition, easier access to the Internet has facilitated and lowered the cost of distributing digital data. As a consequence, even ordinary individuals can now create and distribute copies of digital images easily and inexpensively for purposes beyond private use. Accordingly, though the handling of digital images does not pose a major problem so long as it involves photography for personal enjoyment, the fact that such image data can be copied and distributed easily by unauthorized individuals has not gone unnoticed by those who circulate digital images as a business.

Thus, a problem which arises is that protection of the copyright of photographers, etc., is not satisfactory. Means for protecting copyright is strongly desired for digital image data obtained by photography.

A technique referred to as an "electronic watermark" has undergone extensive research for the purpose of realizing copyright protection of digital image data. This technique is one in which a portion of the data in digital image data or digital audio data is embedded with separate information by superposition in such a manner that the information is rendered insensible or intentionally sensible to a human being, depending upon the particular purpose. When necessary, only a user having the right or qualifications can extract or remove the embedded separate information.

In regard to the principle of electronic watermarking, reference will be had to the specifications of Japanese Patent Application Laid-Open Nos. 10-290359 and 10-150517 to describe, in accordance with FIGS. 9A and 9B, a case where digital information is image information and, moreover, the embedded information is not sensible (or is very nearly insensible) by the user.

FIG. 9A is a diagram illustrating the flow of processing for embedding separate information (embedded data) in image information.

First, an original image (digital image data 401 illustrated in FIG. 10) is divided into a plurality of blocks each of which (block 402 in FIG. 10) is composed of n×m pixels (partitioning processing 901). Next, an orthogonal transform such as a discrete cosine transform (DCT) is applied to each block obtained by division, thereby obtaining an n×m matrix of frequency components (orthogonal transform processing 902).

Before embedding data, an embed component, which indicates in which component of the frequency-component matrix obtained by the orthogonal transform processing the data is to be embedded, is decided based upon a random number, an amount of alteration indicating the extent to which the value of this frequency component will be altered is decided, then the embed component and the amount of alteration are acquired and stored as key information.

By selecting, e.g., a low-frequency portion of the frequency-component matrix as the embed component, the data can be embedded so as not to be sensible by a human being. Further, by changing the amount of alteration, the difference relative to the original value of the frequency-component matrix can be changed. This makes it possible to control the decline in image quality.

The value of the frequency-component matrix of each selected block is changed based upon the embed component and amount of alteration serving as key information 907, thereby embedding embed data 906 (embed processing 903). Furthermore, the frequency-component matrix of each block in which the embed data has been embedded is subjected to an inverse orthogonal transform to obtain an image of a plurality of blocks of n×m pixels each (inverse orthogonal transform processing 904).

Finally, images of the plurality of blocks obtained by the inverse orthogonal transform are connected to obtain a watermark image in which embed data has been embedded (reconstruct processing 905).

FIG. 9B is a diagram illustrating the flow of processing in a case where embed data is extracted from the watermark image. First, the watermark image is divided into a plurality of blocks each of which is composed of n×m pixels (partitioning processing 911). Next, an orthogonal transform such as a discrete cosine transform (DCT) is applied to each block obtained by division, thereby obtaining an n×m matrix of frequency components (orthogonal transform processing 912). Furthermore, the embed component and amount of alteration are obtained from key information 914 that was used at the time of embedding, thereby extracting the embed data from the frequency-component matrix of each block (extraction processing 913).

The watermarking technique according to the above description is advantageous in that (1) the embedded data cannot be extracted without the key information used at the time of embedding; (2) since the embed component in the key information is created based upon a random number, the component is not fixed, thereby making it difficult to decode the embedded data; (3) by specially adapting the embed component, data can be embedded so as not to be sensible by a human being; and (4) the degree to which image quality declines can be controlled by changing the amount of alteration.

An "invisible-data embedding" method through which embedded data is rendered invisible to a human being has been described. As mentioned earlier, however, a "visible-data embedding" method also is available. According to this method, information such as copyright information is embedded in an original image with the intention of being made visible to a human being. This has the effect of causing a third party to abandon the idea of utilizing an image unjustly. For details relating to a visible-data watermarking technique, see the specification of U.S. Pat. No. 5,530,759 (Japanese Patent Application Laid-Open No. 8-241403).

Techniques for authenticating specific individuals are being researched extensively from the standpoint of protecting privacy and providing security.

A number of methods have generally been employed for authenticating individuals. Examples are a method through which only a specific person is verified by a key, card or seal in his or her possession, and a method through which only a specific person is verified by entry of a password or secret code number known only by the person. A fundamental problem with this method is that it is comparatively easy for another person to pose as the specific person by way of theft, counterfeiting or leakage of information, etc.

Accordingly, a method that has become the focus of attention as an alternative to the above method is a biometric personal authentication method that employs a physical characteristic of a specific person to undergo authentication.

It is required that a physical characteristic be unique and person-specific, exhibit randomness and not change over a long period of time. When deployment in an apparatus for performing personal authentication is taken into account, facts to be considered are the time needed to acquire the data needed for authentication and the cost of the apparatus. At the present time, fingerprints, palm prints, iris patterns, voice prints and facial appearance are in wide use as physical characteristics.

Japanese Patent Publication 8-504979 (Japanese translation of PCT International Publication WO94/09446) will be described in general terms with regard to the principle of personal authentication using an iris pattern. FIG. 11 is a flowchart of processing up to a decision as to whether a person being tested is a specific individual or not.

First, the eyeball image of the person is acquired by controlling illumination and focus (1101). When the eyeball image is obtained, the eyelid and eyelash are detected, the pupil-iris boundary 21 and outer boundary 22 of the iris are detected, as shown in FIG. 12, and a coordinate system is set up upon dividing the eyeball into areas 23 referred to as analysis bands (1102).

Next, image analysis (1103), which mainly entails extracting a change in shading of the analysis bands, is performed, and coding is performed based upon the result of analysis (1104). The personal authentication code generated by coding is expressed by a fixed-length array of bits indicated by "1"s and "0"s.

Matching is performed (1105) between the personal authentication code thus coded and a personal authentication code 1107 serving as a template previously acquired from the specific individual. More specifically, the degree of agreement between the two codes is calculated in accordance with a certain evaluation function and, if a fixed threshold value is exceeded, it is decided that the two codes are personal authentication codes sampled from the same individual (1106).

Further, in case of a fingerprint or palm print, the image of the fingerprint or palm print of interest is acquired, the image is coded based upon ridge endings or ridge bifurcations, which are the minutia of the ridges that constitute the fingerprint or palm print, and matching is performed to confirm the individual's identity.

The specification of Japanese Patent Application Laid-Open No. 2000-196998 discloses a method that uses the above-described technique to embed eye information in a photographic image directly as a watermark.

In accordance with this method, an iris pattern or retinal pattern is extracted from an eyeball image acquired at substantially the same time the image of a subject is taken, and the extracted pattern is embedded in the photographic image. As a result, the photographic image and the photographer information are placed in one-to-one correspondence and there is no way for a third party to intervene. This method is effective in that it affords a high reliability as far as copyright information is concerned.

However, the above method necessitates the task of acquiring the eyeball image at approximately the same time that the image of the subject is taken. There are also cases where the method necessitates the additional task of extracting the iris pattern or retinal pattern from the eyeball image and converting this pattern to a personal authentication code by coding means that relies upon image processing. In a digital image sensing device such as a digital still camera, such a task coincides, sequentially speaking, with the timing at which maximum load is imposed upon processing of the subject image at the time of photography. When eyeball-image processing is executed along with subject-image processing, therefore, the overall processing requires a great amount of time. This means that the photographer must wait a while before the next photo can be taken, resulting in possible loss of photographic opportunities.

The imposition of a heavy processing load in this fashion is not limited to a personal authentication method that uses an iris or retinal pattern but is a common problem also in other biometric personal authentication methods that subject personal biological differences to authentication coding by image processing or the like.

When the eyeball image of a photographer is acquired every time an image is taken, the photographer's eye may be closed at the moment of acquisition or an eyelash or strand of hair may interfere. In view of the fact that this can happen frequently, the eyeball image may not always be acquired properly. Furthermore, since the pupil of the photographer's eye opens when an image is taken under low illumination, as is the case indoors, the area of the iris pattern becomes comparatively small and it may not be possible to convert the pattern to an accurate personal authentication code.

Thus, the acquisition of a biological image is affected greatly by the condition of the photographer and surroundings at the time. When the biological image is acquired at the same that an image is taken, an acceptable biological image will not necessarily be obtained. Accordingly, the method of acquiring a biological image at the same time that a subject is photographed is accompanied by considerable disadvantages and risks.

SUMMARY OF THE INVENTION

Accordingly, an object of the present invention is to eliminated the shortcomings mentioned above.

Another object of the present invention is to provide an imaging apparatus that makes it possible to protect the copyright of photographic images by reliably acquiring biological information of a photographer for the purpose of personal authentication and writing this photographer information to the image of a subject without affecting processing, and in a manner transparent to operation, at the time of photography.

According to the present invention, the foregoing object is attained by providing an imaging apparatus for taking an image of a subject by an image sensing device, comprising: registration means for allowing a photographer to register his/her own biological information in advance; storage means for storing the biological information; and personal-data recording means for recording the biological information in a photographic image.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate an embodiment of the invention and, together with the description, serve to explain the principles of the invention.

FIGS. 8A to 8D are operation flowcharts relating to writing of personal data according to this embodiment;

DETAILED DESCRIPTION OF THE PREFERRED EMBODIMENT

A preferred embodiment of the present invention will now be described with reference to the accompanying drawings.

Figure 1:
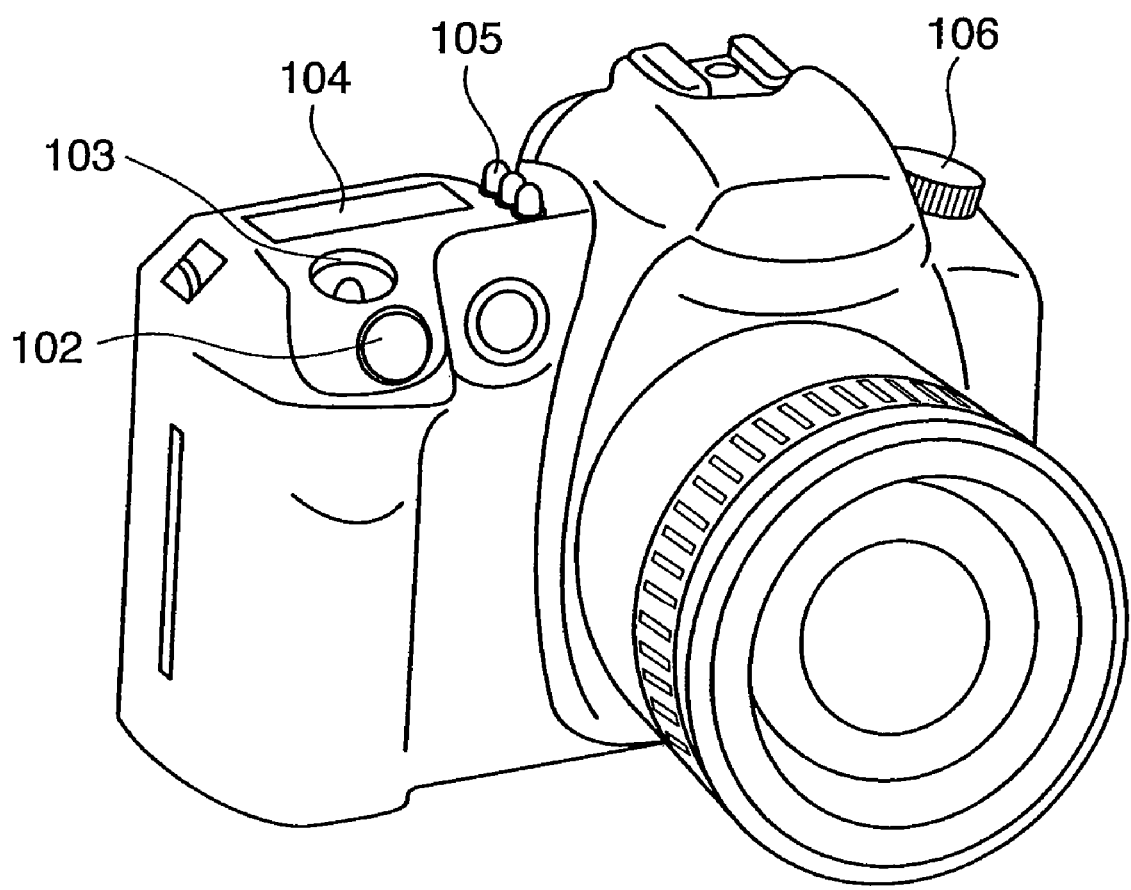
FIG. 1 is a front perspective view illustrating an embodiment of the present invention.

FIG. 1 is a front perspective view of a digital still camera according to an embodiment of the present invention. This embodiment will be described taking as an example a case where a biological-information image to be acquired is an iris image.

Pressing a shutter button 102 on the digital still camera produces a photography-start signal in response to which the image of a subject is captured by an image sensing device. Various settings can be made in response to an input obtained by rotating an electronic dial 103. A liquid crystal panel 104 for displaying photographic information is capable of displaying shutter speed and f-stop value or the set photographic mode, etc. A group 105 of setting buttons is for making various settings. A mode dial 106 is for changing over the mode of photography.

Figure 2:
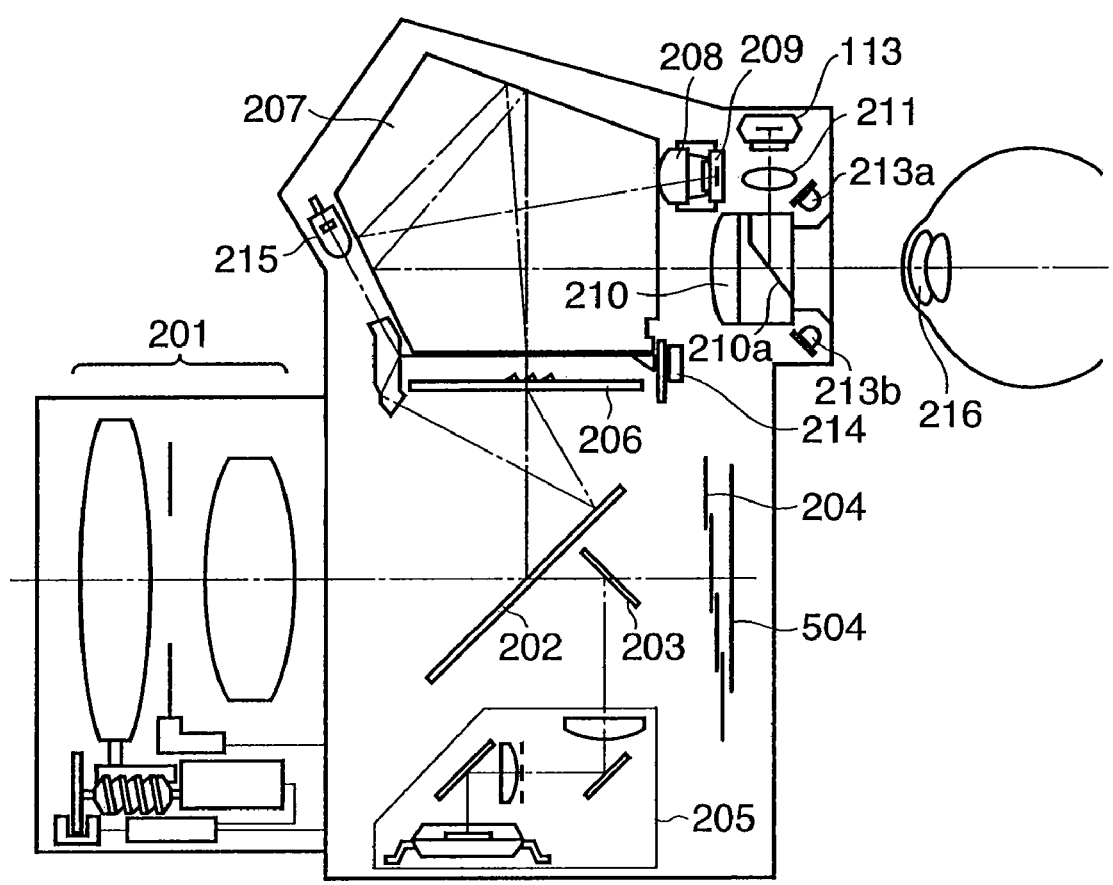
FIG. 2 is a sectional schematic view illustrating a principal portion of this embodiment.

FIG. 2 is a sectional schematic view illustrating a principal portion of the digital still camera according to this embodiment. A group 201 of photographic lenses is shown to be composed of two lenses for the sake of convenience, though a number of lenses are provided in actuality. A main mirror 202 is inclined with respect to the optical path of photography in a case where the camera is in a state for observing the image of the subject by the viewfinder system. The main mirror 202 is retracted from the optical path of photography if the camera is in a state for taking the image of the subject. A subordinate mirror 203 reflects light, which has passed through the main mirror 202, toward a focal-point detector 205 situated at the lower part of the camera body. An image sensing device 504 is a CCD or CMOS area sensor, etc. A shutter 204 opens when the image sensing device 504 is exposed to light.

A focusing plate 206 is disposed on the planned image-forming plane of the photographic lens group 201. A pentagonal prism 207 is for changing the optical path of the viewfinder. An image forming lens 208 and a photometry sensor 209 are for determining judging the luminance of the image of a subject.

An ocular lens 210 having a spectroscope 210a is placed rearwardly of the light-exit side of the pentagonal prism 207 and is used by the photographer to observe the focusing plate 206. The spectroscope 210a comprises, e.g., a dichroic mirror for transmitting visible light and reflecting infrared light.

An iris sensor 113, which employs an image sensing device such as a CCD, is placed so as to become the conjugate of the pupil 216 of the photographer's eye situated at a prescribed position in relation to a light-receiving lens 211. Infrared light-emitting diodes 213a, 213b illuminate the vicinity of the photographer's pupil. An LCD 214 inside the viewfinder, which is placed at a position where it can be observed by the photographer at the same time that the photographer observes the finder image, displays various settings information, etc. A high-luminance light-emitting diode 215 illuminates a prescribed area on the focusing plate 206.

Light from the iris of the photographer is reflected by the spectroscope 210a and has its image formed by the light-receiving lens 211 on the iris sensor 113, whereby the iris image is obtained.

Figure 3:
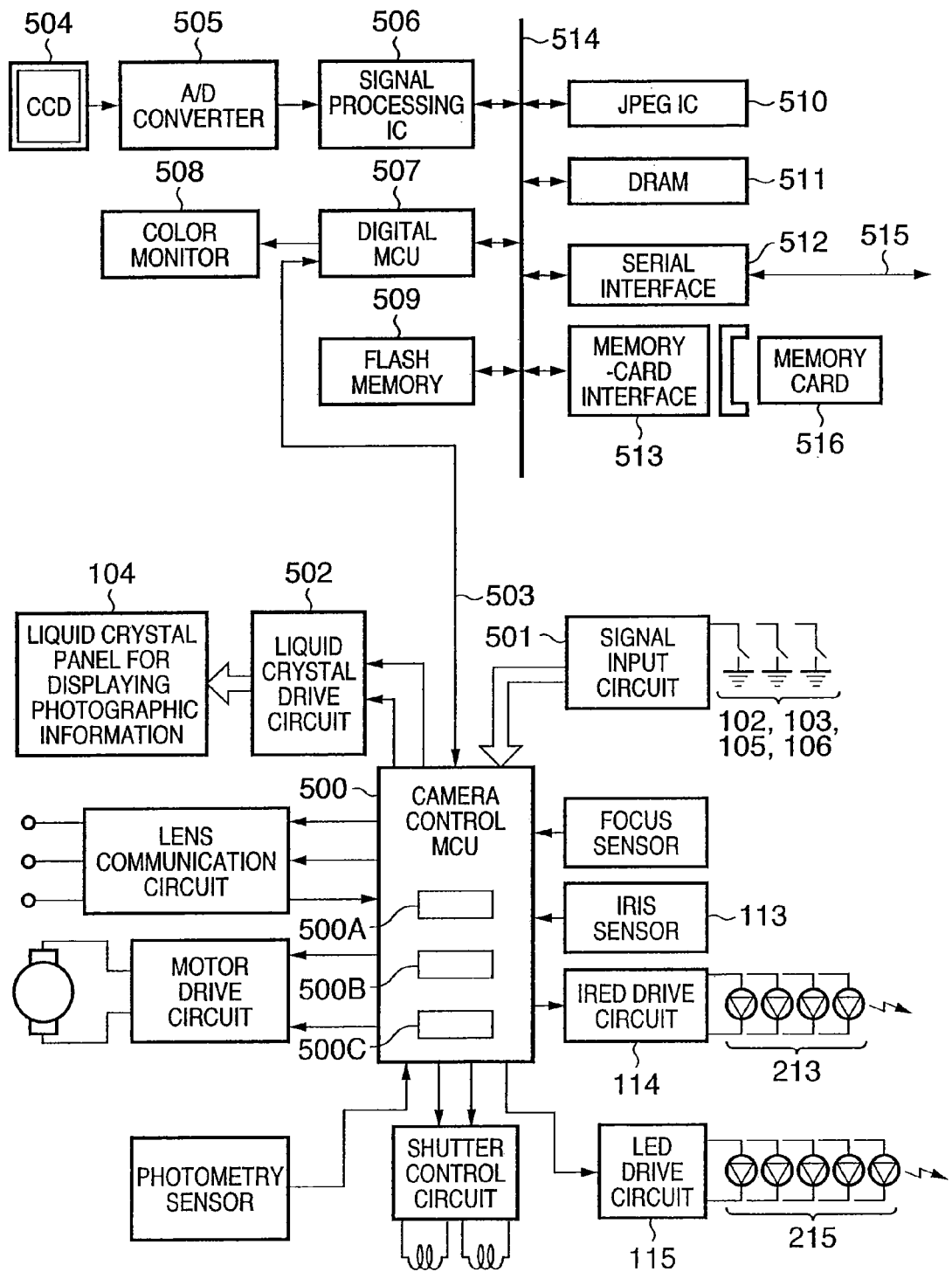
FIG. 3 is a block diagram illustrating the principal electrical circuitry of this embodiment.

FIG. 3 is an electrical block diagram illustrating a digital still camera according to this embodiment. A microcontroller (referred to as an MCU below) 500 is for controlling the camera. Connected to the MCU 500 are camera control circuits and sensors such as the iris sensor 113, an IRED drive circuit 114 for driving the infrared light-emitting diodes 213 that illuminate the vicinity of the pupil, an LED drive circuit 115 for driving the high-luminance light-emitting diode 215, a signal input circuit 501 and a liquid crystal drive circuit 502.

Provided internally of the MCU 500 for camera control are a ROM 500A storing a program for executing camera operation, a RAM 500B for storing a variable, and an EEPROM (electrically erasable programmable ROM) 500C for storing correction data and other parameters.

The iris sensor 113 senses the iris of the photographer and transmits the resulting electrical signal to the camera control MCU 500. The latter converts this transmitted analog electrical signal to digital image data and stores this image data in a RAM successively.

The signal input circuit 501 transmits the states of various camera switches to the camera. Signals from the shutter button 102, group 105 of setting buttons and mode dial 106 also are transmitted to the MCU 500 via this circuit.

The liquid crystal drive circuit 502 is capable of displaying various information on the liquid crystal panel 104, which is for displaying photographic information and is disposed on the outside of the camera, in accordance with a command from the MCU 500.

The camera control MCU 500 is connected to a digital MCU 507 by a signal line 503. The digital MCU 507 controls the photography of a digital image in accordance with a command from the camera control MCU 500. The digital MCU 507 controls various devices relating to photography in accordance with a program stored beforehand in a flash memory 509. By pressing the shutter button 102, the image of a subject is formed on the image sensing device 504, the analog output signal whereof is subjected to an A/D conversion by an A/D converter 505. The resulting digital data is subjected to color interpolation processing and filtering processing, etc., by a signal processing IC 506, after which the processed data is stored temporarily in a DRAM 511 via a data bus 514.

The digital image data that has been stored in the DRAM is displayed on a color monitor 508 when necessary.

The digital image data is integrated with copyright information through a method described later, after which the resulting data is compressed by a JPEG IC 510. The compressed image data is written to a memory card 516, which serves as a removable recording medium, via a memory-card interface 513. Further, the image data can also be output to a serial bus 515 via a serial interface 512.

<Iris Registration Mode>

In the registering of iris information, it is necessary to select the iris registration mode by setting the mode dial 106 of the camera to the REG position. The position of the mode dial 106 and the iris registration mode will be described.

Figure 5:
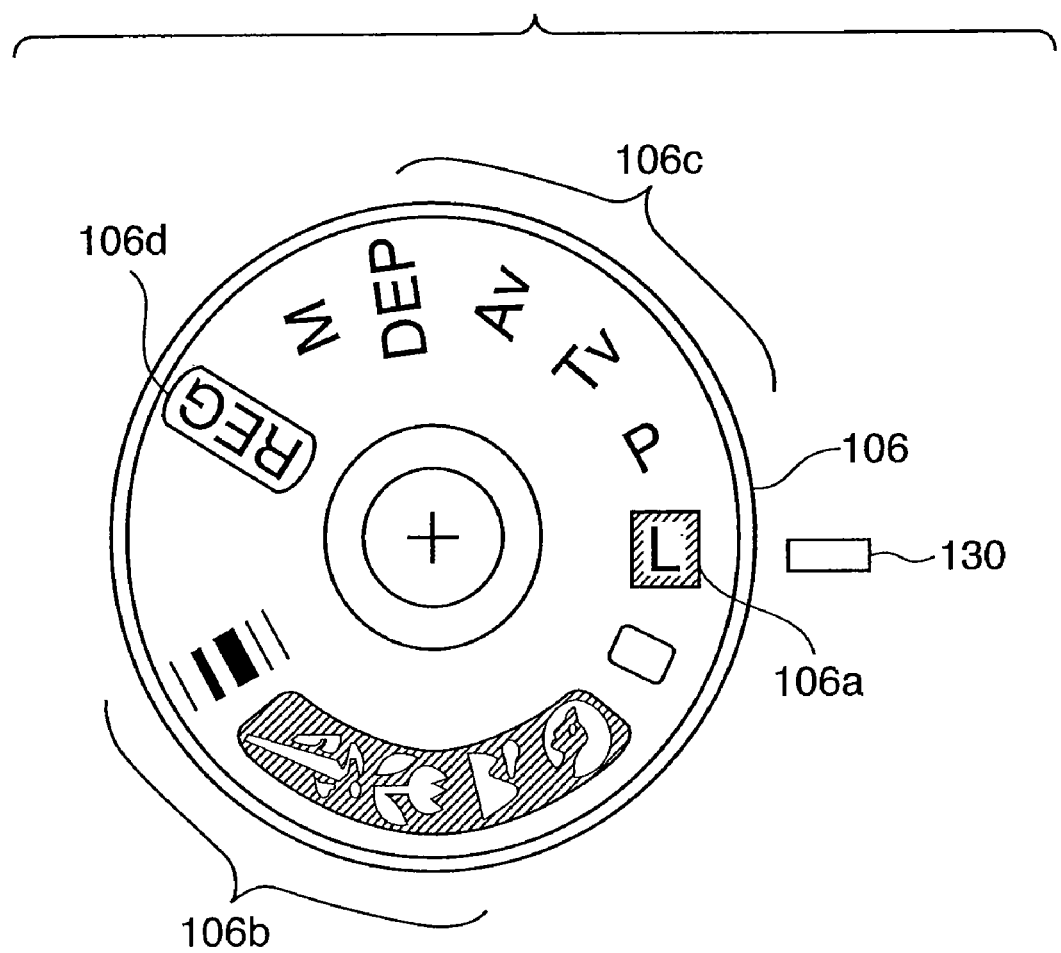
FIG. 5 is a diagram of a mode dial.

FIG. 5 is a detailed view of the mode dial 106 of FIG. 1 when viewed from the top of the camera. When an indication on the mode dial 106 is set to an index marker 130 formed on the camera body, the mode of photography is set based upon the nature of the indication. A position 106a indicates a locking position for rendering the camera inoperable. This indicates that the power supply has been turned off. The camera starts operating in response to the mode dial 106 being turned to a position other than the locking position 106a. A position 106b is for setting the mode of photography to an automatic photography mode in which the camera is controlled by a photography program configured in advance, and a position 106c is for setting the mode of photography to a manual photography mode in which the photographer can set the details of photography. The manual photography mode includes various modes of photography, such as program AE, shutter priority AE, f-stop priority AE, subject depth-of-field priority AE and manual exposure. A position 106d is a "REG" position for setting the mode of photography to the iris registration mode. This is the mode in which the photographer's iris information is registered.

Figure 6:
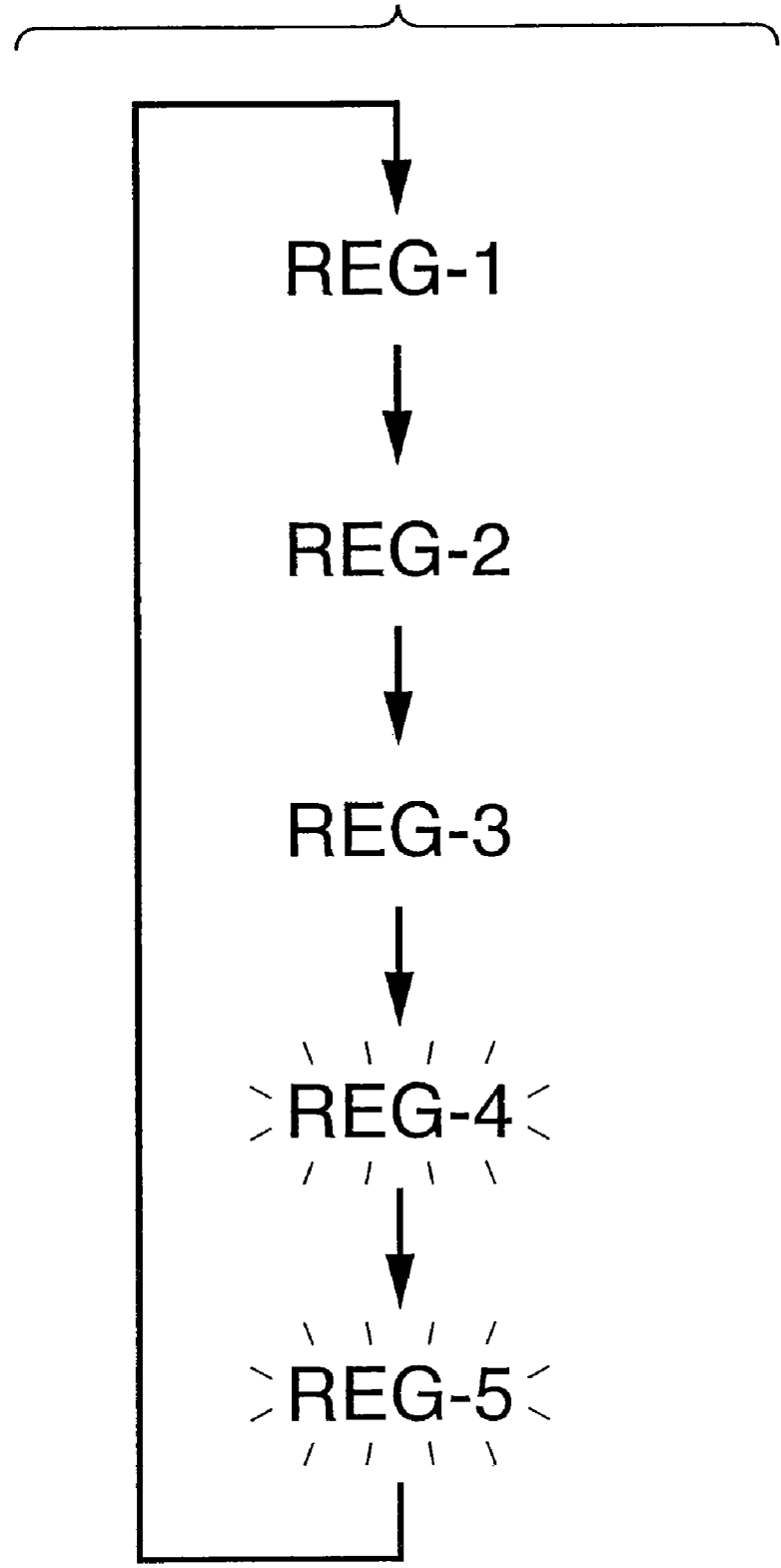
FIG. 6 is a diagram useful in describing display states.

In the iris registration mode, a registration number is selected by turning the electronic dial 103. When the electronic dial 103 is turned clockwise, the registration number changes as follows in dependence upon the amount of rotation (number of clicks of the dial): "REG-1"→"REG-2"→"REG-3"→"REG-4"→"REG-5". The registration number is useful when a number of photographers use the camera. The number is made to correspond to registered content in such a manner that each photographer can register his/her iris information. The iris information of the photographer is registered in association with the registration number selected. The registration number is displayed on the liquid crystal panel 104 for displaying photographic information and on the LCD 214 in the viewfinder. A photographer can store iris information for any desired one of five registration number. This registration number is displayed on the liquid crystal panel 104 for displaying photographic information and on the LCD 214 in the viewfinder. An example of display of registration number is as shown in FIG. 6. The illustrated example shows the manner in which the display transitions from REG-1 to REG-5 in accordance with rotation of the electronic dial 103. "REG-1", "REG-2", "REG-3" are displayed in ordinary fashion, and REG-4, REG-5 are displayed in a flashing manner. This indicates that iris information has already been registered for REG-1 to REG-3, which are not flashing, and that nothing has been registered for "REG-4", "REG-5", which are flashing. A photographer can newly register iris information corresponding to a registration number that is flashing. However, if there is a registration number for which iris information has already been registered, this already registered iris information can be erased and new iris information stored in its place. If the electronic dial 103 is rotated one further click from the REG-5 indication, the display returns to "REG-1". Registration numbers are displayed cyclically in accordance with rotation of the electronic dial 103 in this fashion. If the electronic dial 103 is rotated counter-clockwise, then the order in which the registration numbers are displayed is reversed.

If the mode dial 106 is changed over to another mode of photography while any of "REG-1" to "REG-5" is being displayed, then subsequent processing will be executed using the iris information corresponding to this registration number.

Figure 7:
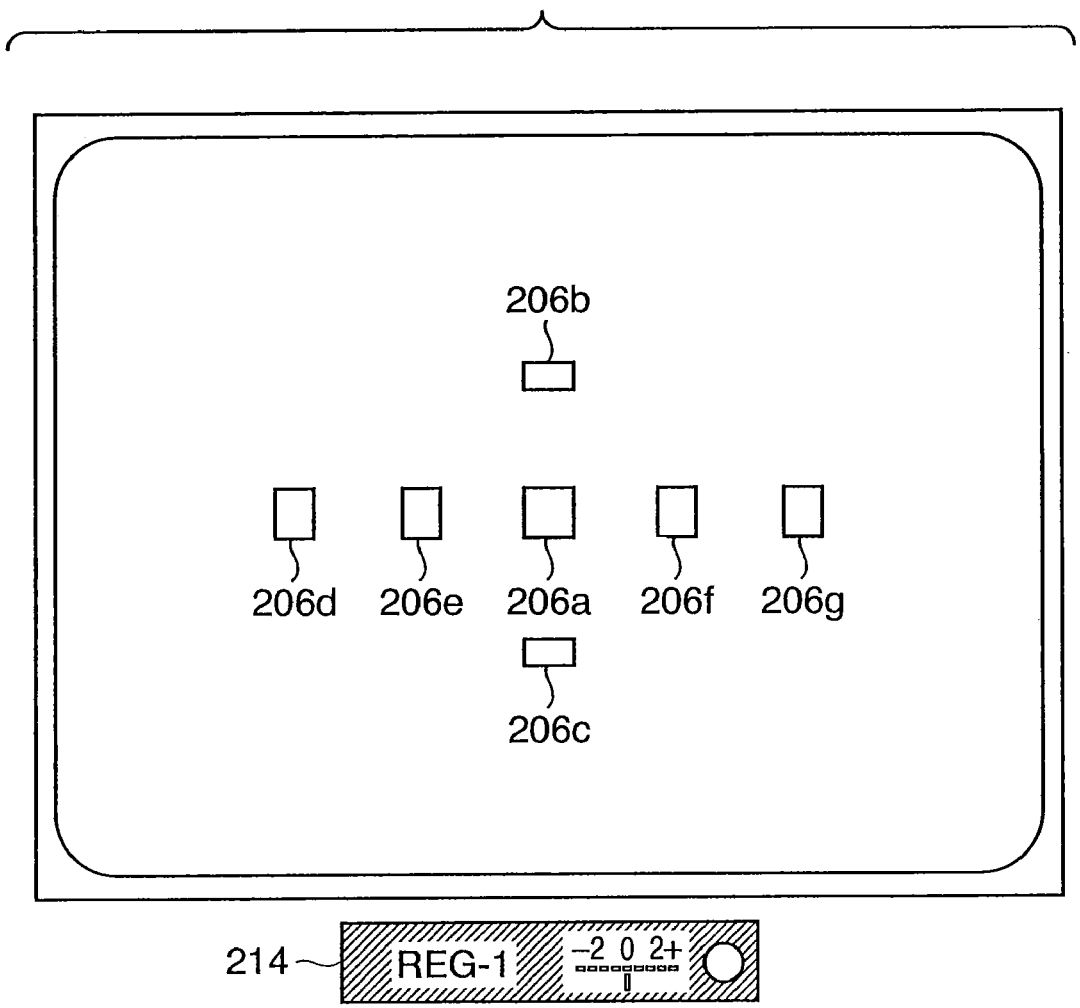
FIG. 7 is a diagram illustrating what is observed in a viewfinder.

The manner in which a photographer observes the viewfinder will be described with reference to FIG. 7. Areas 206a to 206e in FIG. 7 are focus detecting areas written on the focusing plate 206. Detection of focus is possible in a space corresponding to any one of the areas 206a to 206e. In order to notify the photographer of the area selected, the selected area is lit in the viewfinder by the high-luminance light-emitting diode 215. Emission of light in any one area shall be referred to as "superimposing" in this embodiment. The LCD 214 in the viewfinder displays the set state of the camera. This display makes it possible to notify the photographer of which state has been set. The displayed state includes the selected registration number as well ("REG-1" in FIG. 7).

<Processing for Registering Iris Information>

Figure 4:
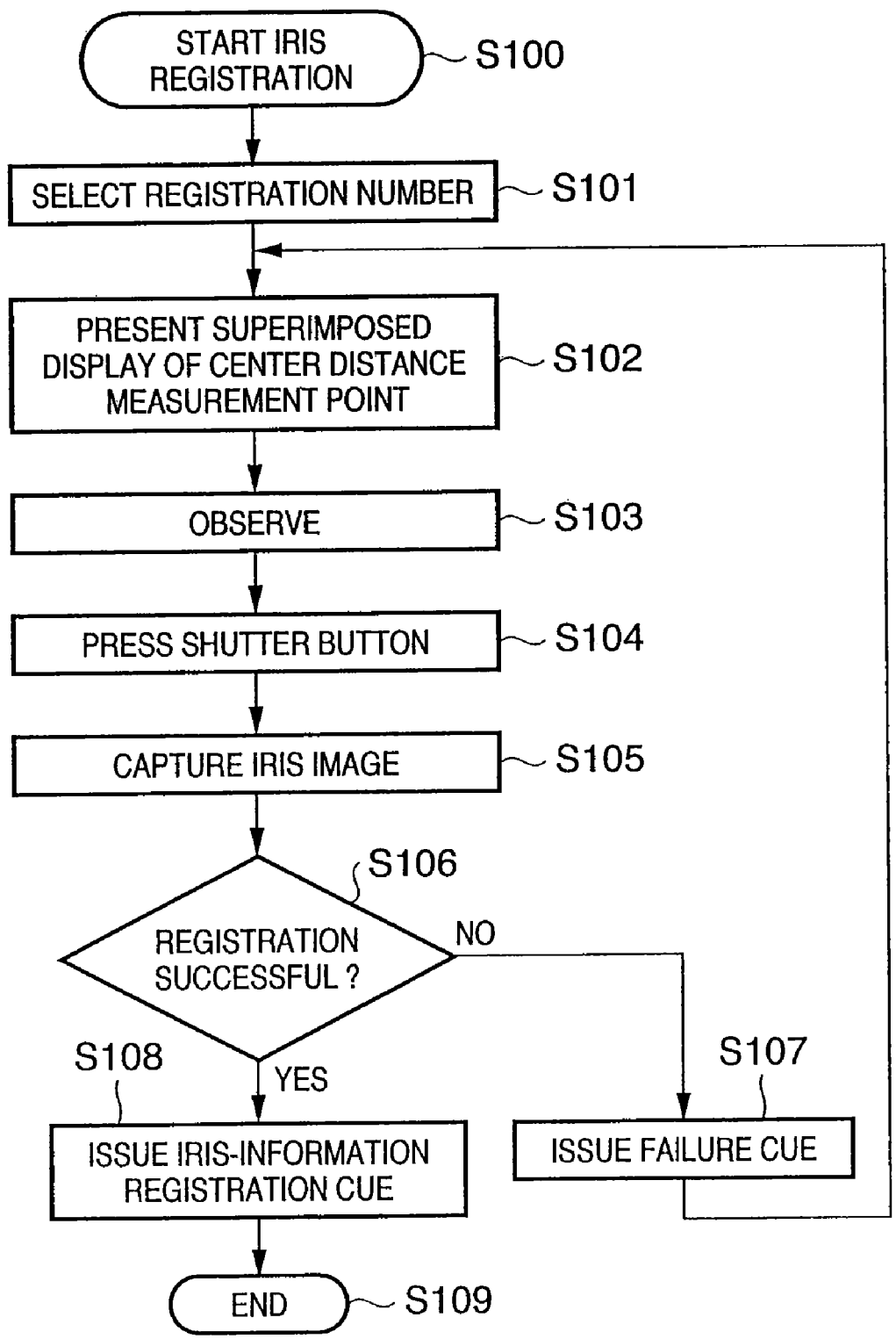
FIG. 4 is an operation flowchart relating to registration of iris information according to this embodiment.

FIG. 4 is a flowchart illustrating the flow of processing for registering photographer iris information in the digital still camera according to this embodiment. The processing of FIG. 4 is executed by the camera control MCU 500 in accordance with an operation performed by the photographer.

At step 100 in FIG. 4, the photographer sets the mode dial 106 to the "REG" position to start iris registration. When the photographer sets the mode dial 106 to the "REG" position 106d at step 100, the processing of FIG. 4 starts.

The registration number selected by the photographer using the electronic dial 103 is selected at step S101 as a registration number for which iris information is registered anew.

If a registration number has been selected at step S101, control proceeds to step S102, where a transition is made to a routine for actually acquiring the iris information of the photographer. The registration number selected at step S101 is displayed on the LCD 214 in the viewfinder, as shown in FIG. 7, and area 206a, which is the focus detection area at the center of the viewfinder, is superimposed at the same time.

Steps S103 and S104 are implemented by the photographer. The photographer gazes at the centrally located focus detection area 206a at step S103 and presses the shutter button 102 at step S104 while gazing at the area 206a. When the shutter button 102 is pressed, the camera captures the photographer's iris image reflected by the spectroscope 210a and formed by the light-receiving lens 211 on the iris sensor 113 (S105). The captured iris image is registered through processing described later. The data to be registered is image data per se (inclusive of a case where the image has been compressed) or data that has been converted to an authentication code based upon the result of image analysis, etc. Registration is performed using the RAM 500B or EEPROM 500C incorporated in the camera control MCU 500.

It is determined at step S106 whether iris information has been acquired acceptably to such a degree that it is satisfactory as personal data indicative of the photographer, i.e., to such a degree that an identity match can be discriminated. If the iris information has not been acquired acceptably, then a cue indicative of failure is presented at step S107. For example, an electronic tone is issued or the fact that acquisition failed is displayed on the LCD 214 in the viewfinder. Control then returns to step S102. If it is determined at step S106 that acquisition was performed acceptably, control proceeds to step S108. Here a cue (display or audio output) indicating that registration succeeded is presented to notify the photographer that registration of iris information has ended.

FIGS. 8A to 8D are flowcharts illustrating a series of photography sequences that start when the camera power supply is turned on. These flowcharts illustrate variations regarding the timing at which iris information of a photographer is written to a photographic image as personal data. The processing of FIGS. 8A to 8D is executed by the digital MCU 507.

FIG. 8A illustrates processing for writing iris information (referred to simply as "personal data" below), which serves as personal identification information, in sync with a command to remove the memory card. Step S200 of this flowchart calls for operation of the camera to be started by turning the mode dial 106 from the locking position 106a to another position. Control then proceeds to step S201. If it is necessary for the photographer to change the registration number to the number at which his/her own iris information has been registered, then the photographer turns the mode dial 106 to the REG position 106d temporarily and then selects the registered number (S202) in the manner described above.

Next, at step S203, an image is taken by the camera through a well-known operation. Specifically, if the shutter button 102 of the camera is pressed, the subject undergoes photometry and photometry processing is executed to decide the exposure value. In addition, the camera is adjusted to bring the subject into focus. If the exposure value has been decided and focusing completed, the image of the subject is formed on the image sensing device 504. This is followed by read-out of the subject image and signal processing and storage of the processed data temporarily in the DRAM 511. Then, following JPEG compression processing, the resulting image data representing the subject is stored in the flash memory 509, thereby ending the imaging operation.

If a command for removing the memory card is applied to the camera by the photographer after the end of this series of imaging operations but before the shutter button is pressed next ("YES" at step S204), i.e., if a locking button (not shown) that prevents removal of the memory card is released, personal data is written to the captured imaged data (referred to simply as a photographic image) in sync with issuance of the card-removal command (S205). The data is written by means described later.

The photographic image (data) that has been recorded in the flash memory is written into the DRAM 511 temporarily, and the personal data that has also been read into the DRAM 511 is combined with or attached to the photographic image to thereby be written to the photographic image. After the personal data is written to the photographic image, a display indicating that removal of the memory card is permissible is presented on the liquid crystal panel 104 for display of photographic information, then the power supply is turned off following elapse of a fixed period of time (step S206).

FIG. 8B is for a case where writing of the personal data is executed in sync with a command to turn off the power supply. The processing of steps S200 to S203 is the same as that of steps S200 to S203 in FIG. 8A and need not be described again.

If a command for turning off the power supply is applied to the camera by the photographer after the end of the series of imaging operations at step S203 but before the shutter button is pressed next ("YES" at step S207), i.e., if the mode dial 106 is set at the locking position 106a, then the personal data is written to the photographic image in sync with issuance of the command (step S205). This is performed by means described later. If writing is finished, the power supply is turned off to place the camera in the inoperable state.

Figure 8C:
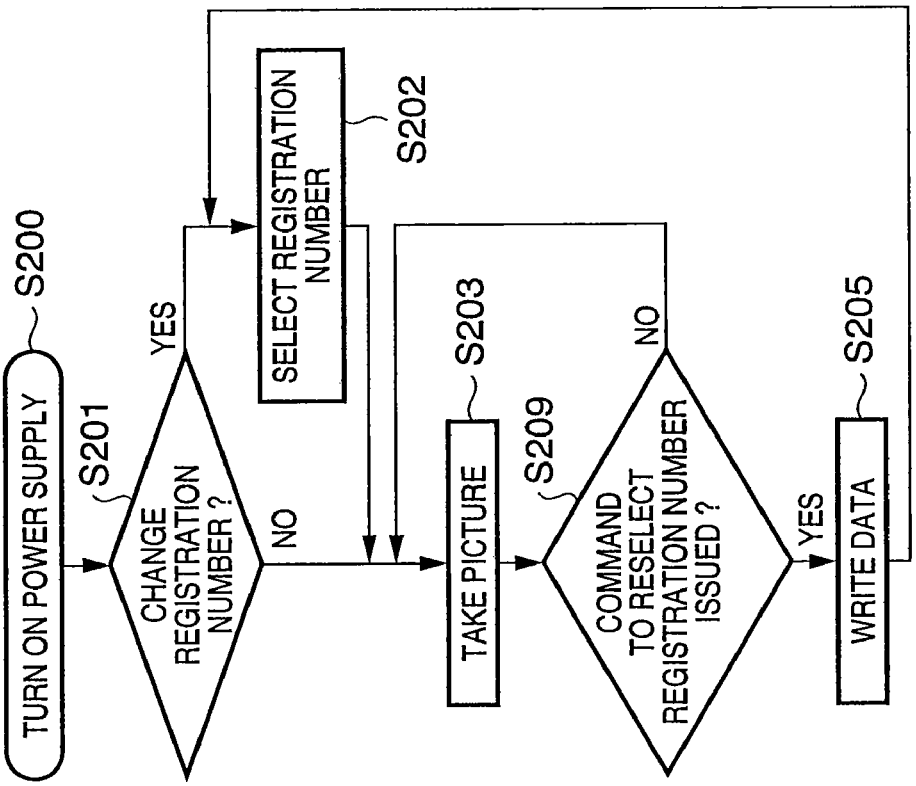

FIG. 8C is for a case where writing of the personal data is executed in sync with a transfer command to transfer a photographic image to another image receiving apparatus such as a personal computer. The processing of steps S200 to S203 is the same as that of steps S200 to S203 in FIG. 8A and need not be described again.

If a command for transferring the photographic image is applied to the camera by the photographer after the end of the series of imaging operations at step S203 but before the shutter button is pressed next ("YES" at step S208), i.e., if a signal for starting output of the photographic image is applied to the serial bus 515 via the serial interface 512 by operating the setting switches 105 and electronic dial 103, then the personal data is written to the photographic image in sync with issuance of the command (step S205). This is performed by means described later. In this case, control returns to step S203, where the camera waits for the next image to be taken, following the end of transfer. It should be noted that the method of image transfer is described here as being by output at the serial bus. However, if the camera is equipped with other transfer means, time timing will be the same as that of the transfer command.

Figure 8D:
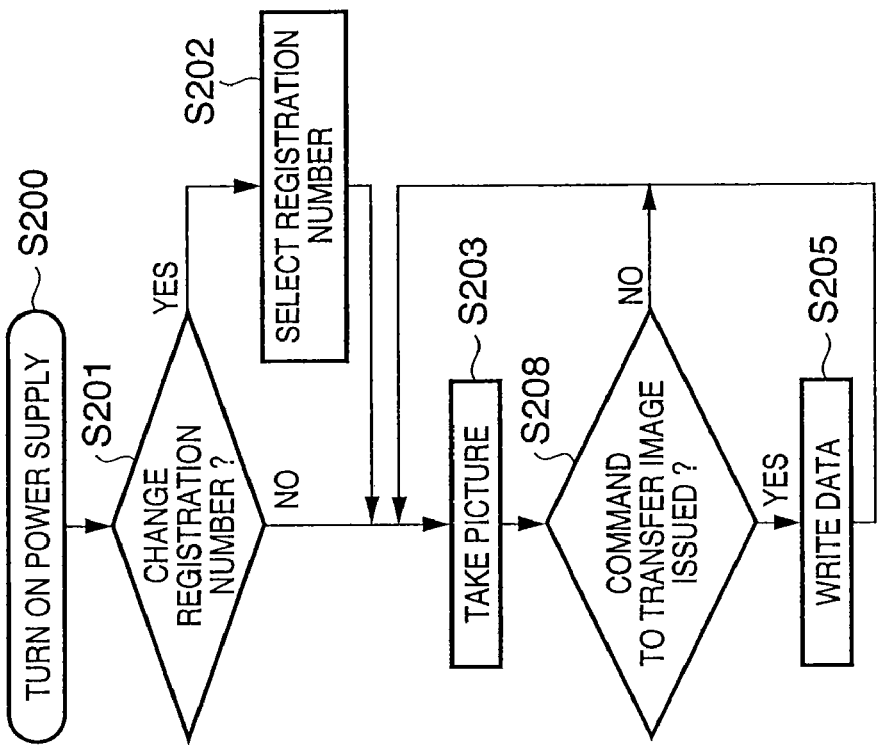
Figure 9A:
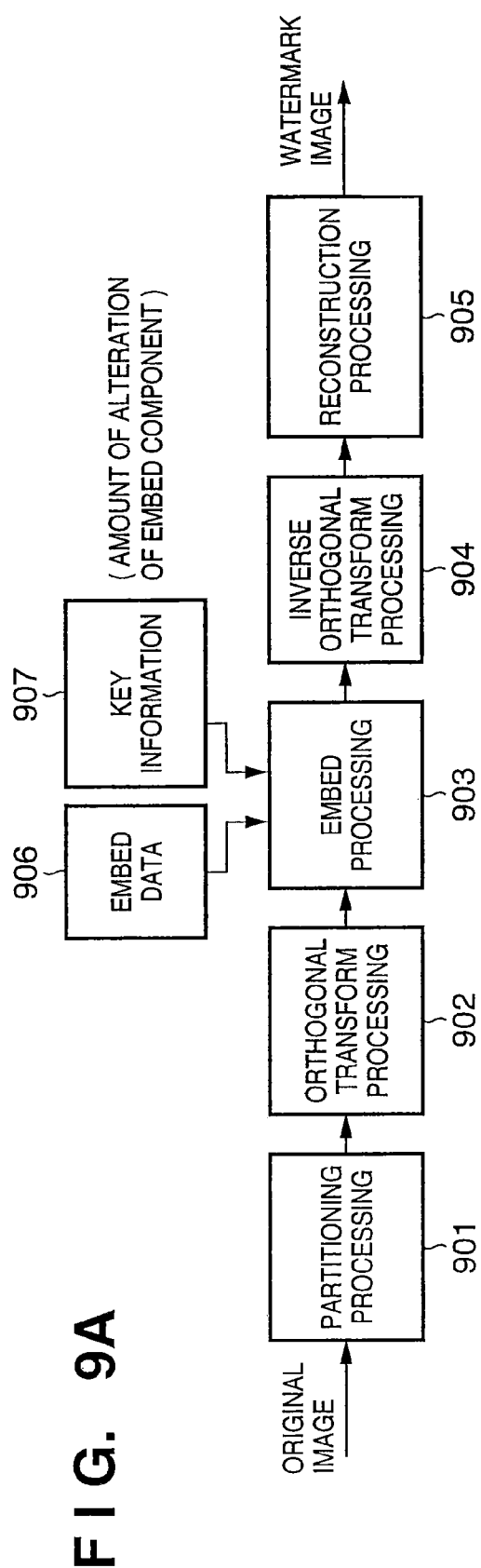
FIGS. 9A and 9B are processing diagram relating to writing of a watermark.
Figure 9B:
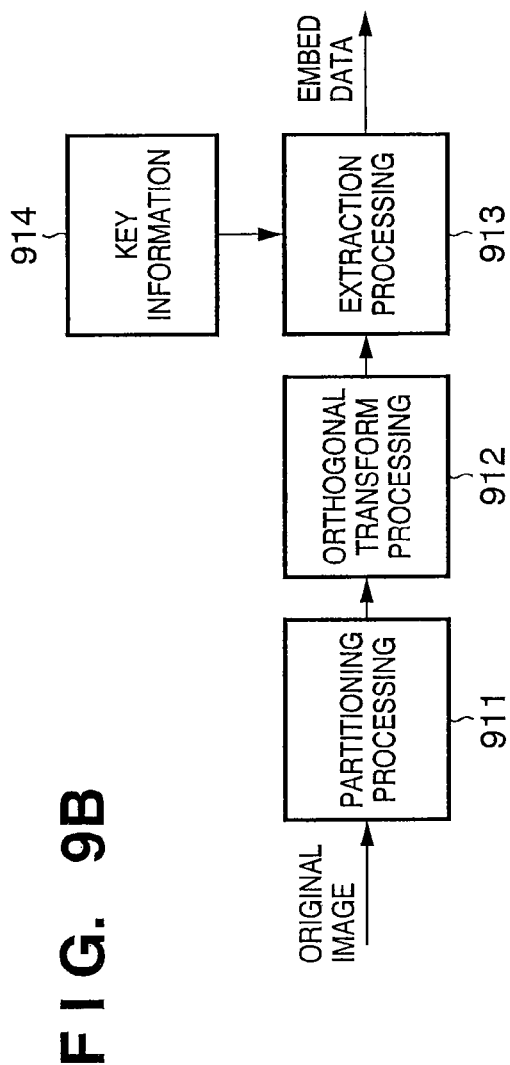
Figure 10:
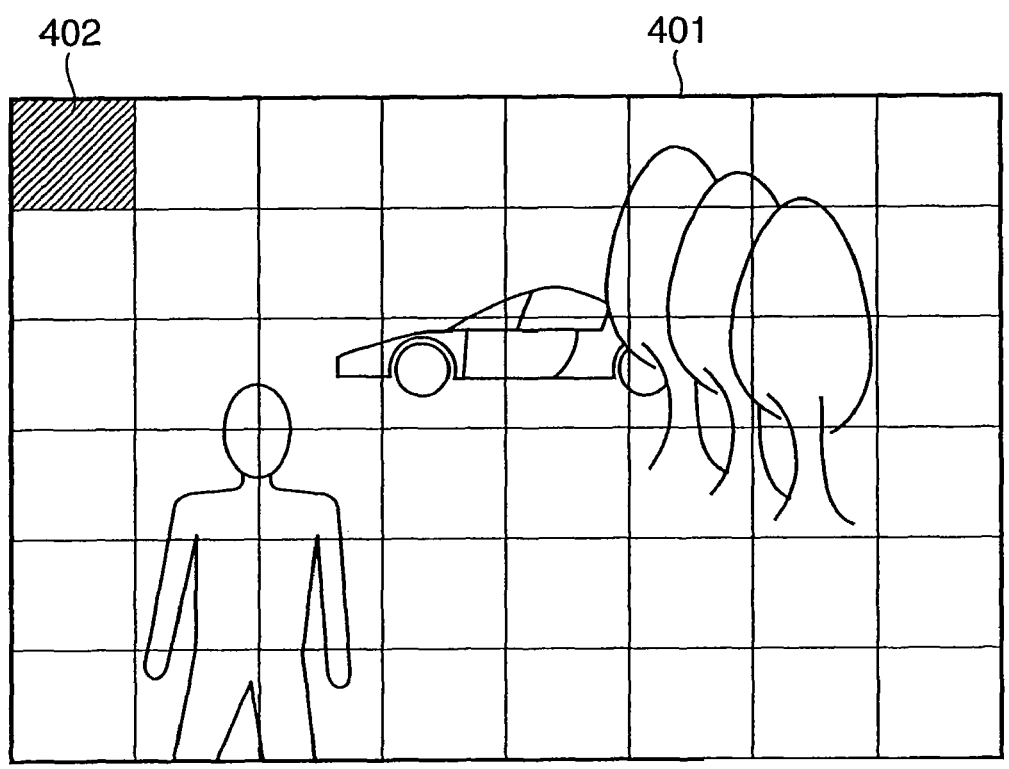
FIG. 10 is a diagram showing the partitioning of an image relating to writing of a watermark.

FIG. 8D is for a case where writing of the personal data is executed in sync with a registration-number reselect command, which is a command for changing to a registration number at which other iris information has been registered. The processing of steps S200 to S203 is the same as that of steps S200 to S203 in FIG. 8A and need not be described again.

If the registration number of iris information is reselected by the photographer after the end of the series of imaging operations at step S203 but before the shutter button is pressed next ("YES" at step S209), i.e., if the photographer turns the electronic dial 103 upon setting the mode dial 106 to the REG position 106d, then the personal data is written to the photographic image by this operation (S205). This is performed by means described later. In this case, after the personal data is written, the registration number is set to the registration number that was selected by the photographer (S202), then control returns to step S203, where the camera waits for the next image to be taken.

<Recording of Personal Identification Data in Photographic Image>

Figure 11:
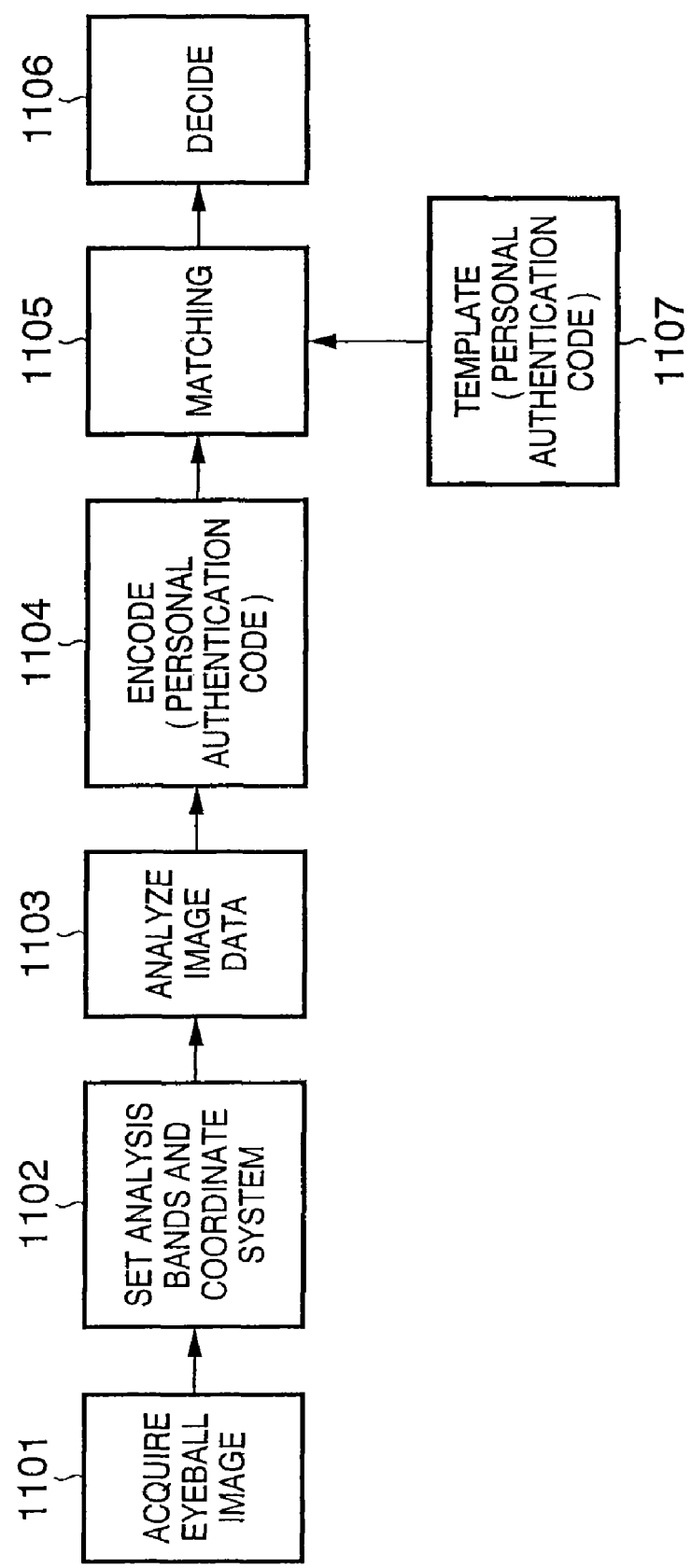
FIG. 11 is a processing diagram relating to personal authentication using an iris image.
Figure 12:
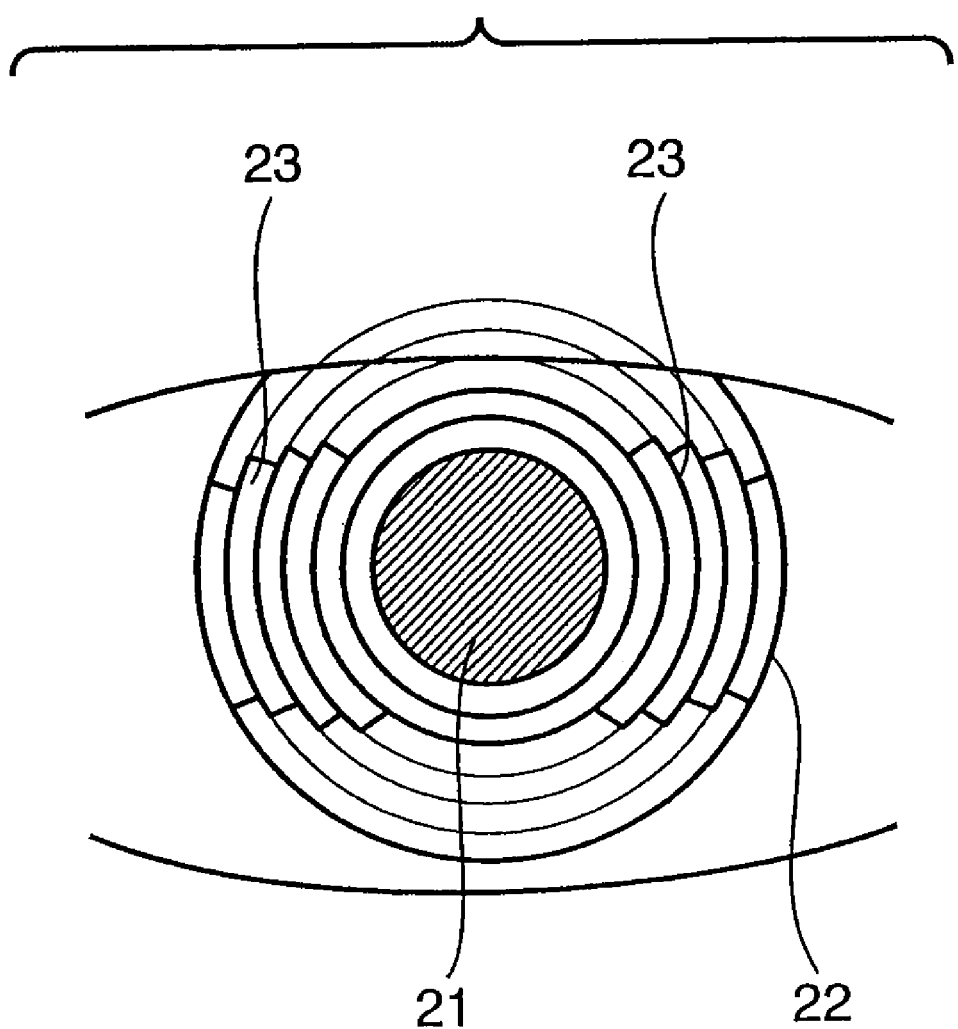
FIG. 12 is a diagram useful in describing the setting of coordinates of an eyeball image.

The means for writing personal data at step S205 in FIGS. 8A to 8D will now be described. In a case where iris information is recorded and registered as personal data, two methods are available. In one method, the iris image acquired by the iris sensor 113 is recorded and registered as biological information in the form of the image per se. In the other method, a personal authentication code, which has been obtained by coding performed through processing in line with the principle of personal authentication based upon an iris pattern described above with reference to FIG. 11, is recorded and registered as the biological information.

In the case where the iris image is registered directly as an image, the iris image is called and expanded temporarily in the DRAM 511, the photographic image to which personal data is to be written also is likewise expanded in the DRAM 511, then processing for embedding the former in the latter as an electronic watermark is executed, thereby achieving writing. This is repeated a number of times equivalent to the number of images taken.

In the case where the iris image is recorded in a state in which it has been processed into a personal authentication code, the code is expressed by a fixed-length array of bits indicated by "1"s and "0"s. The code can therefore be embedded in the photographic image as an electronic watermark through processing similar to that described above. On the other hand, this personal authentication code can also be appended to a photographic image as an item of image metadata added onto the captured image of the subject. In a file-format standard regarding the image of a subject acquired by a digital camera, image metadata is data that has been decided in order to store various attribute information, which is information relating to image data, as one file together with the image data. Examples of the attribute information are date and time of photography, exposure information, mode of photography, image compression rate and white balance, etc. In a case where a personal authentication code is appended as one item of image metadata, only image metadata that has already been added onto a photographic image is expanded in the DRAM 511 to thereby append the personal authentication code. If there is no image metadata, then image metadata is generated anew to append and register a personal authentication code.

In this embodiment, as described above, a photographer's own iris information that the photographer has registered is recorded in a photographic image as personal data. The embedding or addition of personal data to photographic images is performed not each time a frame is shot but collectively at a fixed timing with regard to frames already shot, as shown in FIGS. 8A to 8D. By virtue of this expedient, personal information specific to the photographer, such as iris information, can be embedded in or added to captured digital image data as copyright management information, which is for identifying the person having the rights to copyright material, without attendant processing delay when an image is taken.

As a result of the foregoing, biological information indicative of a photographer need not be acquired every time an image is taken and, hence, processing executed by the imaging apparatus is not subjected to a load in terms of the sequence of photography. Furthermore, biological information can be registered in advance. In a case where information inappropriate for personal authentication could only be acquired, therefore, it is possible to perform registration again. This makes it possible to acquire reliable biological information.

Further, registered biological information indicative of a photographer is recorded in a photographic image attendant upon an operation for turning off a power supply or removing a recording medium, or a command operation for transferring a photographic image to another image receiver, or an operation for reselecting other biological information from multiple items of biological information that have been registered. As a result, processing executed when an image is taken of a subject is not subjected to a load. In other words, congestion can be prevented by recording biological information at a timing at which an image is not being taken.

Further, by recording biological information as an image, coding means or an authentication unit necessary for personal authentication may be provided externally. This reduces the processing to be executed by the imaging apparatus.

Alternatively, by processing an acquired biological image into a personal authentication code and recording the code in the image of a subject, the amount of personal data serving as additional information may be reduced.

Alternatively, by embedding personal data which is biological information in the image of a subject as an electronic watermark, falsification can be prevented more robustly.

Alternatively, biological information may be processed into a personal authentication code and the code may be added on as an item of metadata. In a case where the image of a subject is handled by a third party, therefore, it is easier to deal with a photographer's personal data as copyright information. At the same time, since it is unnecessary to apply processing to the image of a subject per se, there is no decline in image quality.

Further, many digital still cameras are equipped with a liquid crystal display panel in addition to a viewfinder. With a camera of this kind, the photographer can take an image while observing the display on the liquid crystal panel without looking into viewfinder. The camera of the illustrated embodiment is capable of combining personal information with captured digital image data even in a case where the camera takes images through this method.

Modifications of this Embodiment (1) The above embodiment has been described in connection with a digital still camera of the single-lens reflex type. However, as long as the apparatus is of the type that a user operates by looking into a viewfinder, the present invention is applicable to an imaging apparatus such as a digital camera or digital video camera of the type in which the viewfinder is constructed from an independent optical system.

(2) Further, the above embodiment relates to a case where an image representing acquired biological information is iris information. However, the image may be a fingerprint image or palm-print image processed in a manner similar to iris information in the process from acquisition of the biological image to the decision regarding personal identification.

(3) Further, the digital still camera according to this embodiment has a mechanism for accepting a photographer's biological information. However, the effects of this embodiment can be obtained even if the camera has a function for accepting biological information from an external device and combining this information with digital image data. In this case, it would be possible to utilize an electronic signature as the personal information.

(4) Further, the embodiment cites the timings indicated in FIGS. 8A to 8D as examples of the timings at which personal information is combined with digital image data (these timings shall be referred to simply as "recording timing" below). The recording timings may be any of those shown in FIGS. 8A to 8D or the timings of FIGS. 8A to 8D may be combined. However, since FIG. 8A is for a case where the power supply is turned off, FIGS. 8B and 8C cases where digital image data is output and FIG. 8D a case where the photographer is changed, it is desired that the personal information be combined with the digital image data and printed at all of the recording timings illustrated in FIGS. 8A to 8D.

(5) This embodiment has a structure for reading out digital image data that has been recorded temporarily on a recording medium such as a flash memory and combining this data with personal information. However, digital image data of the maximum number of frames allowed by the DRAM 511 can be stored in the DRAM 511. Then, when the upper limit of the DRAM capacity is reached, the digital image data that has been stored in the DRAM at this time can be combined with personal information and the result can be recorded on a recording medium such as the flash memory. The image data in the DRAM is erased after recording is achieved. In this case, it is necessary to combine the digital image data and personal information at the four recording timings shown in FIGS. 8A to 8D. The processing load at the time of photography can be alleviated even further by adopting this expedient.

The present invention can be applied to a system constituted by a plurality of devices (e.g., a host computer, interface, reader, printer, etc.) or to an apparatus comprising a single device (e.g., a copier or facsimile machine, etc.).

Further, it goes without saying that the object of the invention is attained also by supplying a storage medium (or recording medium) on which the program codes of the software for performing the functions of the foregoing embodiment to a system or an apparatus have been recorded, reading the program codes with a computer (e.g., a CPU or MPU) of the system or apparatus from the storage medium, and then executing the program codes.

In this case, the program codes read from the storage medium themselves implement the novel functions of the embodiment, and the program codes per se and storage medium storing the program codes constitute the invention.

Further, besides the case where the aforesaid functions according to the embodiment are implemented by executing the program codes read by a computer, it goes without saying that the present invention covers a case where an operating system or the like running on the computer performs a part of or the entire process based upon the designation of program codes and implements the functions according to the embodiment.

It goes without saying that the present invention further covers a case where, after the program codes read from the storage medium are written in a function expansion card inserted into the computer or in a memory provided in a function expansion unit connected to the computer, a CPU or the like contained in the function expansion card or function expansion unit performs a part of or the entire process based upon the designation of program codes and implements the function of the above embodiment.

In accordance with the present invention, as described above, an imaging apparatus has recording means for recording a photographer's biological information. This makes it unnecessary to acquire biological information and does not subject processing to load in terms of the sequence of photography.

Since biological information is registered, counterfeiting is difficult and reliability is enhanced.

Furthermore, biological information can be registered in advance. In a case where information inappropriate for personal authentication could only be acquired, therefore, it is possible to perform registration again. This makes it possible to acquire reliable biological information.

As many apparently widely different embodiments of the present invention can be made without departing from the spirit and scope thereof, it is to be understood that the invention is not limited to the specific embodiments thereof except as defined in the appended claims.

What is claimed is:

1. An imaging apparatus, comprising:
storage means for storing biological information of a user;
image capturing means for capturing a first group of images; and
a hardware controller that attaches the biological information to each image in the first group of images when a transfer of the first group of images from the imaging apparatus to an external device is instructed by a user after the first group of images is captured by the image capturing means and before a second group of images is captured by the image capturing means.

2. An imaging apparatus, comprising:
a storage unit that stores biological information of a user;
an image sensing device that captures a first group of images; and
a hardware controller that attaches the biological information to each image in the first group of images when a transfer of the first group of images from the imaging apparatus to an external device is instructed by a user after the first group of images is captured by the image sensing device and before a second group of images is captured by the image sensing device.

3. The imaging apparatus according to claim 1, wherein the biological information is attached as personal information to each image in the first group of images.

4. The imaging apparatus according to claim 1, wherein the biological information includes an authentication code generated from an iris pattern of the user.

5. The imaging apparatus according to claim 1, wherein the imaging apparatus accepts the biological information from an external apparatus.

6. The imaging apparatus according to claim 1, wherein the imaging apparatus includes one of a digital camera and a digital video camera.

7. The imaging apparatus according to claim 2, wherein the biological information is attached as personal information to each image in the first group of images.

8. The imaging apparatus according to claim 2, wherein the biological information includes an authentication code generated from an iris pattern of the user.

9. The imaging apparatus according to claim 2, wherein the imaging apparatus accepts the biological information from an external apparatus.

10. The imaging apparatus according to claim 2, wherein the imaging apparatus includes one of a digital camera and a digital video camera.

11. A method comprising the steps of:
storing biological information of a user in a storage unit included in an imaging apparatus;
controlling an image sensing device included in the imaging apparatus to capture a first group of images; and
attaching the biological information to each image in the first group of images when a transfer of the first group of images from the imaging apparatus to an external device is instructed by a user after the first group of images is captured by the image sensing device and before a second group of images is captured by the image sensing device.

12. The method according to claim 11, wherein the biological information is attached as personal information to each image in the first group of images.

13. The method according to claim 11, wherein the biological information includes an authentication code generated from an iris pattern of the user.

14. The method according to claim 11, further comprising:
a step of accepting the biological information from an external apparatus.

15. The method according to claim 11, wherein the imaging apparatus includes one of a digital camera and a digital video camera.

16. The imaging apparatus according to claim 1, wherein a watermarking technique is used to attach the biological information to each image in the first group of images.

17. The imaging apparatus according to claim 2, wherein a watermarking technique is used to attach the biological information to each image in the first group of images.

18. The method according to claim 11, wherein a watermarking technique is used to attach the biological information to each image in the first group of images.

* * * * *